United States Patent
Bartholomäus et al.

(10) Patent No.: US 8,114,383 B2
(45) Date of Patent: *Feb. 14, 2012

(54) ABUSE-PROOFED DOSAGE FORM

(75) Inventors: Johannes Bartholomäus, Aachen (DE);
Heinrich Kugelmann, Aachen (DE);
Elisabeth Arkenau-Marić, Köln (DE)

(73) Assignee: Gruenenthal GmbH, Aachen (DE)

(*) Notice: Subject to any disclaimer, the term of this patent is extended or adjusted under 35 U.S.C. 154(b) by 325 days.

This patent is subject to a terminal disclaimer.

(21) Appl. No.: 10/718,112

(22) Filed: Nov. 20, 2003

(65) Prior Publication Data

US 2005/0031546 A1    Feb. 10, 2005

(30) Foreign Application Priority Data

Aug. 6, 2003   (DE) .................................. 103 36 400

(51) Int. Cl.
*A61K 49/00* (2006.01)
(52) U.S. Cl. .................................. 424/10.1; 424/10.4
(58) Field of Classification Search .................. 424/10.1
See application file for complete search history.

(56) References Cited

U.S. PATENT DOCUMENTS

| | | |
|---|---|---|
| 3,806,603 A | 4/1974 | Gaunt et al. |
| 3,865,108 A | 2/1975 | Hartop |
| 3,966,747 A | 6/1976 | Monkovic |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. ............. 424/2 |
| 4,070,497 A | 1/1978 | Wismer |
| 4,175,119 A * | 11/1979 | Porter ........................... 424/475 |
| 4,207,893 A | 6/1980 | Michaels |
| 4,262,017 A | 4/1981 | Kuipers |
| 4,343,789 A | 8/1982 | Kawata et al. |
| 4,353,887 A | 10/1982 | Hess |
| 4,404,183 A | 9/1983 | Kawata et al. |
| 4,427,681 A | 1/1984 | Manshi |
| 4,462,941 A | 7/1984 | Lee |
| 4,603,143 A | 7/1986 | Schmidt |
| 4,612,008 A | 9/1986 | Wong et al. .................. 604/892 |
| 4,629,621 A | 12/1986 | Snipes |
| 4,690,822 A | 9/1987 | Uemura et al. |
| 4,713,243 A | 12/1987 | Schiraldi et al. |
| 4,744,976 A | 5/1988 | Snipes et al. |
| 4,764,378 A | 8/1988 | Keith et al. |
| 4,765,989 A | 8/1988 | Wong et al. .................. 424/473 |
| 4,774,074 A | 9/1988 | Snipes |
| 4,783,337 A | 11/1988 | Wong et al. .................. 424/468 |
| 4,806,337 A | 2/1989 | Snipes et al. |
| RE33,093 E | 10/1989 | Schiraldi et al. |
| 4,880,585 A | 11/1989 | Klimesch |
| 4,892,778 A | 1/1990 | Theeuwes et al. |
| 4,892,889 A | 1/1990 | Kirk |
| 4,940,556 A | 7/1990 | MacFarlane |
| 4,957,668 A | 9/1990 | Plackard |
| 4,957,681 A | 9/1990 | Klimesch |
| 4,960,814 A | 10/1990 | Wu |
| 4,992,278 A | 2/1991 | Khanna |
| 4,992,279 A | 2/1991 | Palmer |
| 5,004,601 A | 4/1991 | Snipes |
| 5,051,261 A | 9/1991 | McGinity et al. |
| 5,169,645 A | 12/1992 | Shukla |
| 5,198,226 A | 3/1993 | MacFarlane |
| 5,200,197 A | 4/1993 | Wright et al. |
| 5,211,892 A | 5/1993 | Gueret et al. |
| 5,273,758 A | 12/1993 | Royce |
| 5,350,741 A | 9/1994 | Takada |
| 5,378,462 A | 1/1995 | Boedecker |
| 5,427,798 A | 6/1995 | Ludwig |
| RE34,990 E | 7/1995 | Khanna |
| 5,458,887 A | 10/1995 | Chen |
| 5,460,826 A | 10/1995 | Merrill et al. |
| 5,556,640 A | 9/1996 | Ito et al. |
| 5,562,920 A | 10/1996 | Demmer et al. |
| 5,601,842 A | 2/1997 | Bartholomaeus |
| 5,620,697 A | 4/1997 | Tormala et al. |
| 5,681,517 A | 10/1997 | Metzger |
| 5,792,474 A | 8/1998 | Rauchfuss |
| 5,801,201 A | 9/1998 | Graudums et al. |
| 5,811,126 A | 9/1998 | Krishnamurthy |
| 5,849,240 A * | 12/1998 | Miller et al. .................. 264/460 |
| 5,866,164 A * | 2/1999 | Kuczynski et al. ........... 424/472 |
| 5,916,584 A | 6/1999 | O'Donoghue |
| 5,928,739 A | 7/1999 | Pophusen |
| 5,945,125 A | 8/1999 | Kim |
| 5,948,787 A | 9/1999 | Merrill et al. |
| 5,968,925 A | 10/1999 | Knidlberger |
| 6,009,390 A | 12/1999 | Gupta et al. |
| 6,009,690 A | 1/2000 | Rosenberg |
| 6,077,538 A | 6/2000 | Merrill |
| 6,096,339 A | 8/2000 | Ayer et al. |
| 6,117,453 A | 9/2000 | Seth et al. |
| 6,133,241 A | 10/2000 | Bok |
| 6,228,863 B1 | 5/2001 | Palermo et al. |
| 6,235,825 B1 | 5/2001 | Yoshida |
| 6,238,697 B1 * | 5/2001 | Kumar et al. .................. 424/464 |
| 6,245,357 B1 | 6/2001 | Edgren et al. |
| 6,248,737 B1 | 6/2001 | Buschmann et al. |
| 6,261,599 B1 | 7/2001 | Oshlack |
| 6,306,438 B1 | 10/2001 | Oshlack et al. |

(Continued)

FOREIGN PATENT DOCUMENTS

AR    46994    12/2004

(Continued)

OTHER PUBLICATIONS

Zhang et al. (Pharm. Dev. Tech. 1999, 4, 241-250).*

(Continued)

*Primary Examiner* — Michael G Hartley
*Assistant Examiner* — Melissa Perreira
(74) *Attorney, Agent, or Firm* — Norris McLaughlin & Marcus, P.A.

(57) ABSTRACT

The present invention relates to an abuse-proofed, thermoformed dosage form containing, in addition to one or more active ingredients with abuse potential optionally together with physiologically acceptable auxiliary substances, at least one synthetic or natural polymer with a breaking strength of at least 500 N and to a process for the production thereof.

9 Claims, No Drawings

U.S. PATENT DOCUMENTS

| | | | |
|---|---|---|---|
| 6,309,668 B1 | 10/2001 | Bastin et al. | 424/472 |
| 6,340,475 B2 | 1/2002 | Shell et al. | |
| 6,344,535 B1 | 2/2002 | Timmermann | |
| 6,348,469 B1 | 2/2002 | Seth | |
| 6,375,963 B1 | 4/2002 | Repka et al. | |
| 6,399,100 B1 | 6/2002 | Clancy et al. | |
| 6,419,954 B1 | 7/2002 | Chu | |
| 6,436,441 B1 | 8/2002 | Sako et al. | |
| 6,461,644 B1 | 10/2002 | Jackson | |
| 6,488,962 B1 | 12/2002 | Berner et al. | |
| 6,488,963 B1 | 12/2002 | McGinity et al. | |
| 6,534,089 B1 | 3/2003 | Ayer et al. | |
| 6,547,997 B1 | 4/2003 | Breitenbach et al. | |
| 6,562,375 B1 | 5/2003 | Sako et al. | |
| 6,592,901 B2 | 7/2003 | Durig | |
| 6,635,280 B2 | 10/2003 | Shell et al. | |
| 6,699,503 B1 | 3/2004 | Sako et al. | |
| 6,723,340 B2 | 4/2004 | Gusler et al. | |
| 6,733,783 B2* | 5/2004 | Oshlack et al. | 424/473 |
| 6,753,009 B2 | 6/2004 | Luber et al. | |
| 6,821,588 B1 | 11/2004 | Hammer | |
| 7,141,250 B2 | 11/2006 | Oshlack et al. | |
| 7,176,251 B1 | 2/2007 | Bastioli | |
| 7,776,314 B2 | 8/2010 | Bartholomäus et al. | |
| 2001/0038852 A1 | 11/2001 | Kolter | |
| 2002/0012701 A1 | 1/2002 | Kolter | |
| 2002/0015730 A1 | 2/2002 | Hoffmann | |
| 2002/0051820 A1 | 5/2002 | Shell et al. | |
| 2002/0114838 A1 | 8/2002 | Ayer et al. | |
| 2002/0132359 A1 | 9/2002 | Waterman | |
| 2002/0187192 A1 | 12/2002 | Joshi | |
| 2003/0015814 A1 | 1/2003 | Krull | |
| 2003/0017532 A1 | 1/2003 | Biswas | |
| 2003/0021546 A1 | 1/2003 | Sato | |
| 2003/0031546 A1 | 2/2003 | Araki | |
| 2003/0044458 A1 | 3/2003 | Wright, IV | |
| 2003/0044464 A1 | 3/2003 | Ziegler et al. | |
| 2003/0064099 A1 | 4/2003 | Oshlack et al. | 424/465 |
| 2003/0068392 A1 | 4/2003 | Sackler | 424/760 |
| 2003/0091630 A1 | 5/2003 | Louie-Helm et al. | |
| 2003/0104052 A1 | 6/2003 | Berner et al. | |
| 2003/0118641 A1 | 6/2003 | Maloney et al. | 424/465 |
| 2003/0124185 A1 | 7/2003 | Oshlack et al. | 424/465 |
| 2003/0125347 A1 | 7/2003 | Anderson et al. | |
| 2003/0133985 A1 | 7/2003 | Louie-Helm et al. | |
| 2003/0152622 A1 | 8/2003 | Louie-Helm et al. | |
| 2003/0158242 A1 | 8/2003 | Kugelmann | |
| 2003/0175326 A1 | 9/2003 | Thombre | |
| 2003/0232895 A1 | 12/2003 | Omidian | |
| 2004/0010000 A1 | 1/2004 | Ayer et al. | |
| 2004/0011806 A1 | 1/2004 | Luciano | |
| 2004/0052844 A1 | 3/2004 | Hsiao et al. | |
| 2004/0081694 A1 | 4/2004 | Oshlack | |
| 2004/0091528 A1 | 5/2004 | Rogers | |
| 2004/0131671 A1 | 7/2004 | Zhang | |
| 2004/0156899 A1 | 8/2004 | Louie-Helm et al. | |
| 2004/0170567 A1* | 9/2004 | Sackler | 424/10.1 |
| 2004/0185105 A1 | 9/2004 | Berner et al. | |
| 2004/0213848 A1 | 10/2004 | Li et al. | |
| 2005/0015730 A1 | 1/2005 | Gunturi et al. | |
| 2005/0031546 A1 | 2/2005 | Bartholomaus et al. | |
| 2005/0058706 A1 | 3/2005 | Bartholomaus | |
| 2005/0063214 A1 | 3/2005 | Takashima | |
| 2005/0089475 A1 | 4/2005 | Gruber | |
| 2005/0095291 A1 | 5/2005 | Oshlack et al. | |
| 2005/0106249 A1 | 5/2005 | Hwang et al. | |
| 2005/0112067 A1 | 5/2005 | Kumar et al. | |
| 2005/0127555 A1 | 6/2005 | Gusik | |
| 2005/0152843 A1 | 7/2005 | Bartholomaus | |
| 2005/0186139 A1 | 8/2005 | Bartholomaus | |
| 2005/0191244 A1 | 9/2005 | Bartholomaus | |
| 2005/0214223 A1 | 9/2005 | Bartholomaeus | |
| 2005/0236741 A1 | 10/2005 | Arkenau | |
| 2005/0266084 A1 | 12/2005 | Li et al. | |
| 2006/0002859 A1 | 1/2006 | Arkenau | |
| 2006/0002860 A1 | 1/2006 | Bartholomaus | |
| 2006/0039864 A1 | 2/2006 | Bartholomaus | |
| 2006/0099250 A1 | 5/2006 | Tian | |
| 2006/0188447 A1 | 8/2006 | Arkenau-Maric | |
| 2006/0193782 A1 | 8/2006 | Bartholomaus | |
| 2006/0193914 A1 | 8/2006 | Ashworth | |
| 2006/0240110 A1 | 10/2006 | Kiick et al. | |
| 2007/0003616 A1 | 1/2007 | Arkenau-Maric | |
| 2007/0020188 A1 | 1/2007 | Sackler | |
| 2007/0020335 A1 | 1/2007 | Chen et al. | |
| 2007/0048228 A1 | 3/2007 | Arkenau-Maric | |
| 2007/0065365 A1 | 3/2007 | Kugelmann | |
| 2007/0092573 A1 | 4/2007 | Joshi et al. | |
| 2007/0183979 A1 | 8/2007 | Arkenau-Maric | |
| 2007/0183980 A1 | 8/2007 | Arkenau-Maric | |
| 2007/0190142 A1 | 8/2007 | Breitenbach | |
| 2007/0196396 A1 | 8/2007 | Pilgaonkar et al. | |
| 2007/0196481 A1 | 8/2007 | Amidon | |
| 2007/0264327 A1 | 11/2007 | Kumar et al. | |
| 2007/0269505 A1 | 11/2007 | Flath et al. | |
| 2008/0081290 A1 | 4/2008 | Wada | |
| 2008/0247959 A1 | 10/2008 | Bartholomaus | |
| 2008/0248113 A1 | 10/2008 | Bartholomaus | |
| 2008/0311049 A1 | 12/2008 | Arkenau-Maric | |
| 2008/0311187 A1 | 12/2008 | Ashworth | |
| 2008/0311197 A1 | 12/2008 | Arkenau-Maric | |
| 2008/0312264 A1 | 12/2008 | Arkenau-Maric | |
| 2008/0317854 A1 | 12/2008 | Arkenau | |
| 2009/0004267 A1 | 1/2009 | Arkenau-Maric | |
| 2009/0005408 A1 | 1/2009 | Arkenau-Maric | |
| 2009/0081290 A1 | 3/2009 | McKenna | |
| 2009/0202634 A1 | 8/2009 | Jans | |
| 2010/0015223 A1 | 1/2010 | Cailly-Dufestel | |
| 2010/0098758 A1 | 4/2010 | Bartholomaus et al. | |
| 2010/0151028 A1 | 6/2010 | Ashworth et al. | |
| 2010/0221322 A1 | 9/2010 | Bartholomaus et al. | |
| 2010/0260833 A1 | 10/2010 | Bartholomaus et al. | |
| 2011/0020451 A1 | 1/2011 | Bartholomaus et al. | |
| 2011/0038930 A1 | 2/2011 | Barnscheid et al. | |
| 2011/0082214 A1 | 4/2011 | Faure et al. | |

FOREIGN PATENT DOCUMENTS

| | | |
|---|---|---|
| AR | 045353 | 10/2005 |
| AR | 049562 | 8/2006 |
| AR | 053304 | 5/2007 |
| AR | 054222 | 6/2007 |
| AR | 054328 | 6/2007 |
| AU | 2003237944 | 12/2003 |
| AU | 2003274071 | 5/2004 |
| AU | 2003278133 | 5/2004 |
| AU | 2003279317 | 5/2004 |
| AU | 2004264666 | 2/2005 |
| AU | 2004264667 | 2/2005 |
| AU | 2004308653 | 4/2005 |
| AU | 2005259476 | 1/2006 |
| AU | 2005259478 | 1/2006 |
| AU | 2006210145 | 8/2006 |
| AU | 2009207796 | 7/2009 |
| AU | 2009243681 | 11/2009 |
| BR | P10413318 | 10/2006 |
| BR | P10413361 | 10/2006 |
| BR | P10513300 | 5/2008 |
| BR | P10606145 | 2/2009 |
| CA | 2317747 A1 | 7/1999 |
| CA | 2352874 A1 | 6/2000 |
| CA | 250 2965 A1 | 5/2004 |
| CA | 2534925 | 2/2005 |
| CA | 2534932 | 2/2005 |
| CA | 2551231 | 7/2005 |
| CA | 2572352 | 1/2006 |
| CA | 2572352 A1 | 1/2006 |
| CA | 2572491 | 1/2006 |
| CA | 2595954 | 7/2006 |
| CA | 2595979 | 8/2006 |
| CA | 2713128 | 7/2009 |
| CA | 2723438 | 11/2009 |
| CH | 689109 A5 | 10/1998 |
| CN | 1980643 | 4/2005 |
| CN | 101010071 | 6/2005 |
| CN | 101022787 | 1/2006 |
| CN | 001863513 | 11/2006 |
| CN | 001863514 | 11/2006 |

| | | | | | | |
|---|---|---|---|---|---|---|
| CN | 01917862 | 2/2007 | EP | 0857062 A2 | 8/1998 |
| CN | 101027044 | 8/2007 | EP | 0864324 A1 | 9/1998 |
| CN | 101111232 | 1/2008 | EP | 0864326 A2 | 9/1998 |
| CN | 101175482 | 2/2008 | EP | 0 980 894 A1 | 9/1999 |
| DE | 2530 563 | 1/1977 | EP | 0988106 A1 | 3/2000 |
| DE | 2808505 A1 | 9/1978 | EP | 1014941 A1 | 7/2000 |
| DE | 4309528 | 3/1993 | EP | 1070504 A1 | 1/2001 |
| DE | 43 09 528 | 9/1994 | EP | 1127871 A1 | 8/2001 |
| DE | 69400215 T2 | 10/1996 | EP | 1138321 A2 | 10/2001 |
| DE | 19522899 C1 | 12/1996 | EP | 1166776 A2 | 1/2002 |
| DE | 19753534 | 12/1997 | EP | 1251120 A1 | 10/2002 |
| DE | 19800698 | 1/1998 | EP | 1293127 A2 | 3/2003 |
| DE | 19822979 | 5/1998 | EP | 1293196 A2 | 3/2003 |
| DE | 19753534 A1 | 6/1999 | EP | 1250045 B1 | 9/2003 |
| DE | 19800689 C1 | 7/1999 | EP | 1658055 | 2/2005 |
| DE | 19800698 A1 | 7/1999 | EP | 1515702 | 3/2005 |
| DE | 19822979 A1 | 12/1999 | EP | 1527775 A1 | 4/2005 |
| DE | 69229881 T2 | 12/1999 | EP | 1558221 A1 | 8/2005 |
| DE | 0980894 | 2/2000 | EP | 1558257 | 8/2005 |
| DE | 19856147 A1 | 6/2000 | EP | 1560585 | 8/2005 |
| DE | 19940740 A1 | 3/2001 | EP | 1658054 | 5/2006 |
| DE | 19960494 A1 | 6/2001 | EP | 1740161 | 1/2007 |
| DE | 10036400 A1 | 6/2002 | EP | 1765303 | 3/2007 |
| DE | 19855440 A1 | 6/2002 | EP | 1786403 | 5/2007 |
| DE | 69429710 T2 | 8/2002 | EP | 1558221 B1 | 6/2007 |
| DE | 10250083 A1 | 12/2003 | EP | 1845955 | 10/2007 |
| DE | 10250084 A1 | 5/2004 | EP | 1845956 | 10/2007 |
| DE | 10250087 A1 | 5/2004 | EP | 1 859 789 | 11/2007 |
| DE | 10250088 | 5/2004 | EP | 1897545 A1 | 12/2008 |
| DE | 10336400 A1 | 3/2005 | EP | 2131830 | 12/2009 |
| DE | 102004019916 | 11/2005 | EP | 2249811 | 11/2010 |
| DE | 102004020220 | 11/2005 | EP | 2273983 | 1/2011 |
| DE | 10 2004 032049 A1 | 1/2006 | ES | 2336571 | 12/2004 |
| DE | 10 2004 032051 A1 | 1/2006 | ES | 2260042 T3 | 11/2006 |
| DE | 10 2004 032103 A1 | 1/2006 | ES | 2285497 | 11/2007 |
| DE | 10 2005 005446 A1 | 8/2006 | ES | 2288621 | 1/2008 |
| DE | 10 2005 005449 A1 | 8/2006 | ES | 2289542 | 2/2008 |
| DE | 102007011485 | 9/2008 | ES | 2315505 | 4/2009 |
| DK | 1658055 | 7/2007 | GB | 1147210 A | 4/1969 |
| DK | 1658054 | 10/2007 | GB | 2057878 A | 4/1981 |
| DK | 1515702 | 1/2009 | HR | P20070272 | 6/2007 |
| EC | SP066345 | 8/2006 | HR | 20070456 | 11/2007 |
| EP | 0 008 131 | 2/1980 | JP | 3-0501737 A | 4/1991 |
| EP | 0043254 A1 | 1/1982 | JP | 8 505076 | 6/1996 |
| EP | 0177893 A2 | 4/1986 | JP | 8-505076 A | 6/1996 |
| EP | 0 216 453 | 4/1987 | JP | 2002-275175 A | 9/2002 |
| EP | 0 226 061 | 6/1987 | JP | 2005534664 | 11/2005 |
| EP | 0 228 417 | 7/1987 | KR | 1020060069832 | 6/2006 |
| EP | 0229652 A2 | 7/1987 | KR | 20070039041 | 4/2007 |
| EP | 0 232 877 | 8/1987 | KR | 20070111510 | 11/2007 |
| EP | 0240906 A2 | 10/1987 | KR | 20100111303 | 10/2010 |
| EP | 0261616 A2 | 3/1988 | KR | 20110016921 | 2/2011 |
| EP | 0270954 A1 | 6/1988 | MX | 2007000008 | 3/2007 |
| EP | 0 277 289 | 8/1988 | MX | 2007000009 | 3/2007 |
| EP | 0 293 066 | 11/1988 | MX | 2007009393 | 8/2007 |
| EP | 0 328 775 | 8/1989 | MX | 2010008138 | 8/2010 |
| EP | 0477135 A1 | 3/1992 | MX | 2010012039 | 11/2010 |
| EP | 0544144 A1 | 6/1993 | NO | 20061054 | 3/2006 |
| EP | 0 583 726 | 2/1994 | NO | 20070578 | 1/2007 |
| EP | 0 598 606 | 5/1994 | NO | 20074412 | 11/2007 |
| EP | 0636370 A1 | 2/1995 | PT | 1699440 | 12/2004 |
| EP | 0641195 A1 | 3/1995 | PT | 1658054 | 5/2006 |
| EP | 0647448 A1 | 4/1995 | PT | 1658055 | 7/2007 |
| EP | 0682945 A2 | 5/1995 | PT | 1515702 | 12/2008 |
| EP | 0 661 045 | 7/1995 | RU | 2131244 C1 | 6/1999 |
| EP | 0661045 A1 | 7/1995 | RU | 2354357 | 12/2007 |
| EP | 0675710 A1 | 10/1995 | RU | 2007103712 | 9/2008 |
| EP | 0693475 | 1/1996 | RU | 2007103707 | 11/2008 |
| EP | 0693475 A1 | 1/1996 | RU | 2007132975 | 4/2009 |
| EP | 0820693 A1 | 1/1996 | SI | 1515702 | 4/2009 |
| EP | 0 696 598 | 2/1996 | SI | 1699440 | 11/2009 |
| EP | 0756480 A1 | 2/1997 | WO | 89/05624 A1 | 6/1989 |
| EP | 0760654 A1 | 3/1997 | WO | 90 03776 | 4/1990 |
| EP | 0780369 | 6/1997 | WO | 9003776 A1 | 4/1990 |
| EP | 0780369 A1 | 6/1997 | WO | 93 06723 | 4/1993 |
| EP | 0785775 A1 | 7/1997 | WO | 93 10758 A1 | 6/1993 |
| EP | 0809488 A1 | 12/1997 | WO | 93 11749 | 6/1993 |
| EP | 0820698 | 1/1998 | WO | 94 06414 | 3/1994 |
| EP | 0820698 A1 | 1/1998 | WO | 94 08567 A1 | 4/1994 |

| | | |
|---|---|---|
| WO | 95/17174 A1 | 6/1995 |
| WO | 95 22319 A1 | 8/1995 |
| WO | WO 95/20947 | 8/1995 |
| WO | 95 30422 | 11/1995 |
| WO | 96 00066 | 1/1996 |
| WO | 96/03979 A1 | 2/1996 |
| WO | 9614058 A1 | 5/1996 |
| WO | 9733566 | 9/1997 |
| WO | 9820073 | 5/1998 |
| WO | WO 98/20073 | 5/1998 |
| WO | 98 28698 A1 | 7/1998 |
| WO | 98/35655 A2 | 8/1998 |
| WO | 99/12864 A1 | 3/1999 |
| WO | 99 32120 A1 | 7/1999 |
| WO | 99/48481 A1 | 9/1999 |
| WO | 9944591 A1 | 9/1999 |
| WO | WO/00/33835 * | 6/2000 |
| WO | WO0033835 * | 6/2000 |
| WO | 0040205 | 7/2000 |
| WO | 01/12230 A1 | 2/2001 |
| WO | 0108661 A2 | 2/2001 |
| WO | 0115667 A1 | 3/2001 |
| WO | 01/52651 A2 | 7/2001 |
| WO | 01/97783 A1 | 12/2001 |
| WO | 02/26061 A1 | 4/2002 |
| WO | 02/26262 A2 | 4/2002 |
| WO | 02 26928 | 4/2002 |
| WO | 02/088217 A1 | 11/2002 |
| WO | 03 06723 A1 | 1/2003 |
| WO | 03 013476 A1 | 2/2003 |
| WO | 03/013479 A1 | 2/2003 |
| WO | WO 03/015531 | 2/2003 |
| WO | WO 03/015531 A2 | 2/2003 |
| WO | 03 024430 | 3/2003 |
| WO | 03/026624 A1 | 4/2003 |
| WO | 03 026743 A2 | 4/2003 |
| WO | 03/026743 A2 | 4/2003 |
| WO | 03 028698 A2 | 4/2003 |
| WO | 03/028990 A1 | 4/2003 |
| WO | 03/031546 A1 | 4/2003 |
| WO | 03 035029 | 5/2003 |
| WO | 03/035177 A2 | 5/2003 |
| WO | 03035029 A1 | 5/2003 |
| WO | 03035053 A1 | 5/2003 |
| WO | 03035054 A1 | 5/2003 |
| WO | 03053417 A2 | 7/2003 |
| WO | 03/068392 A1 | 8/2003 |
| WO | 03/092648 A1 | 11/2003 |
| WO | 03/094812 A1 | 11/2003 |
| WO | 03 105808 | 12/2003 |
| WO | 2004/004693 A1 | 1/2004 |
| WO | 2004/043967 A1 | 2/2004 |
| WO | 2004 026263 A2 | 4/2004 |
| WO | WO/2004/026262 | 4/2004 |
| WO | WO 2004026262 A2 * | 4/2004 |
| WO | 2004037230 A1 | 5/2004 |
| WO | 2004037259 A1 | 5/2004 |
| WO | 2004037260 A1 | 5/2004 |
| WO | 2004/066910 A2 | 8/2004 |
| WO | 2004/084869 A1 | 10/2004 |
| WO | 2004/093801 A2 | 11/2004 |
| WO | 2004/100894 A2 | 11/2004 |
| WO | 2004093819 A2 | 11/2004 |
| WO | 2005 016313 | 2/2005 |
| WO | 2005 016314 | 2/2005 |
| WO | 2005016314 A1 | 2/2005 |
| WO | 2005/032524 A2 | 4/2005 |
| WO | 2005/065646 A2 | 4/2005 |
| WO | 2005 041968 | 5/2005 |
| WO | 2005/053656 A1 | 6/2005 |
| WO | 2005/055981 A2 | 6/2005 |
| WO | 2005 063214 | 7/2005 |
| WO | 2005/066183 A1 | 7/2005 |
| WO | 2005063214 A1 | 7/2005 |
| WO | 2005 102286 | 11/2005 |
| WO | 2005102286 A1 | 11/2005 |
| WO | 2006 002883 | 1/2006 |
| WO | 2006 002884 | 1/2006 |
| WO | 2006002884 | 1/2006 |
| WO | 2006002886 A1 | 1/2006 |
| WO | 2005102294 | 5/2006 |
| WO | 2006 082097 | 8/2006 |
| WO | 2006 082099 | 8/2006 |
| WO | 2007/005716 A2 | 1/2007 |
| WO | 2007 008752 | 1/2007 |
| WO | 2007 048233 | 5/2007 |
| WO | 2007 053698 | 5/2007 |
| WO | 2007/085024 A2 | 7/2007 |
| WO | 2008/086804 A2 | 7/2008 |
| WO | 2008/107149 A2 | 9/2008 |
| WO | 2008107149 | 9/2008 |
| WO | 2008/148798 A2 | 12/2008 |
| WO | 2009003776 A1 | 1/2009 |
| WO | 2009/092601 A1 | 7/2009 |
| WO | 2009092601 | 7/2009 |
| WO | 2009/135680 A1 | 11/2009 |
| WO | 2009135680 | 11/2009 |
| WO | 2011009602 | 1/2011 |
| WO | 2011009603 | 1/2011 |
| WO | 2011009604 | 1/2011 |

OTHER PUBLICATIONS

Maggi et al. (Biomaterials 2002, 23, 1113-1119).*
DOW Technical Data, POLYOXTIM WSR, Feb. 2003.*
DeJong (Pharmaceutisch Weekblad Scientific Edition 1987, p. 24-28).*
Observations by Third Parties Pursuant to Art 115 EPC, dated Feb. 2, 2009.
Letter of James W. McGinty, with attached experimental report, dated Jan. 26, 2009.
V.K. Thoma et al., "Bestimmung der In-vitro-Freigabe von schwach basischen Wirkstoffen aus Retardarzneiformen," Pharm. Ind. 51, Nr. 3 (1989).
F. E. Bailey et al., "Some Properties of Poly(ethylene oxide) in Aqueous Solution," Journal of Applied Polymer Science, vol. 1, Issue No. 1, pp. 56-62 (1959).
A. Apicella et al., "Poly(ethylene oxide) (PEO) and different molecular weight PEO blends monolithic devices for drug release," Biomaterials 1993, vol. 14, No. 2, pp. 83-90.
S. Janicki et al., "Slow-Release Microballs: Method of Preparation," Acta Pharm. Technol. 33(3) 154-155 (1987).
R. Mank et al., "Darstellung wirkstoffhaltiger Extrusionsformlinge auf der Basis von Thermoplasten," Pharmazie 45 (1990), H. 8; pp. 592-593.
R. Mank et al., "Darstellung wirkstoffhaltiger Extrusionsformlinge auf der Basis von Thermoplasten," Pharmazie 44 (1989) H. 11; pp. 773-776.
P. Shivanand et al., "Factors Affecting Release of KCl from Melt Extruded Polyethylene Disks," Pharmaceutical Research, Official Journal of the American Association of Pharmaceutical Scientists; Oct. 1991, vol. 8, No. 10.
L. Yang et al., "Characterization of Compressibility and Compatibility of Poly(ethylene oxide) Polymers for Modified Release Application by Compaction Simulator," Journal of Pharmaceutical Sciences, vol. 85, No. 10, Oct. 1996.
F. Zhang et al., "Properties of Sustained-Release Tablets Prepared by Hot-Melt Extrusion," Pharmaceutical Development and Technology, 4(2), 241-250 (1999) pp. 241-250.
M.M. Crowley et al., "Stability of polyethylene oxide in matrix tablets prepared by hot-melt extrusion," Biomaterials 23 (2002) 4241-4248.
M. Efentakis et al., "Evaluation of High Molecular Weight Poly(Oxyethylene) (Polyox) Polymer: Studies of Flow Properties and Release Rates of Furosemide and Captopril from Controlled-Release Hard Gelatin Capsules," Pharmaceutical Development and Technology, 5(3), 339-346 (2000).
N. Follonier et al., "Various ways of modulating the release of diltiazem hydrochloride from hot-melt extruded sustained release pellets prepared using polymeric materials," Journal of Controlled Release 36 (1995) 243-250.
N.B. Graham, "Poly(Ethylene Glycol) Gels and Drug Delivery," Poly(Ethylene Glycol) Chemistry: Biotechnical and Biomedical Applications, Chapter 17, 1992.

C. D. Hanning et al., "The Morphine Hydrogel Suppository," British Journal of Anaesthesia, 1988, 61, 221-227.
Kim et al., "Preparation and Evaluation of Eudragit Gels V. Rectal Gel Preparations for Sustained Release and Avoidance of First-Pass Metabolism of Lidocaine," Chem. Pharm. Bull. 40(10) 2800-2804 (1992).
Cherng-Ju Kim, "Drug Release from Compressed Hydrophilic POLYOX-WSR Tablets," Journal of Pharmaceutical Sciences, vol. 84, No. 3, Mar. 1995.
S.L. Madorsky et al., "Thermal Degradation of Polyethylene Oxide and Polypropylene Oxide," Journal of Polymer Science, vol. XXXVI, pp. 183-194 (1959).
A. Moroni et al., "Application of Poly(Oxyethylene) Homopolymers in Sustained Release Solid Formulations," Drug Development and Industrial Pharmacy, 21(12), 1411-1428 (1995).
N. Ohnishi et al., "Effect of the Molecular Weight of Polyethylene Glycol on the Bioavailability of Indomethacin Sustained-Release Suppositories Prepared with Solid Dispersions," Chem. Pharm. Bull., 35 (8) 3511-3515 (1987).
T. Ozeki et al., "Control of medicine release from solid dispersion composed of the poly(ethylene oxide)-carboxyvinylpolymer interpolymer complex by varying molecular weight of poly(ethylene oxide)," Journal of Controlled Release 58 (1999) 87-95.
Pharmaceutical Research, Official Journal of the American Association of Pharmaceutical Scientists, Sep. 1989 (Supplement), vol. 6, No. 9, 6.S-98.
Pharmaceutical Research, Official Journal of the American Association of Pharmaceutical Scientists, Oct. 1991 (Supplement), Vo. 8, No. 10, 8.S-192.
W. Prapaitrakul et al., "Release of Chlorpheniramine Maleate from Fatty Acid Ester Matrix Disks Prepared by Melt-extrusion," J. Pharm. Pharmacol. 1991, 43: 377-381.
S. Radko et al., "Molecular sieving by polymer solutions: dependence on particle and polymer size, independence of polymer entanglement," Applied and Theoretical Electrophoresis (1995), 5, 79-88.
J. Scheirs et al., "Characterizing the solid-state thermal oxidation of poly(ethylene oxide) powder," Polymer, 1991, vol. 32, No. 11.
O.L. Sprockel et al., "Permeability of Cellulose Polymers: Water Vapour Transmission Rates," J. Pharm. Pharmacol. 1990, 42: 152-157.
J.L. Stringer et al., "Diffusion of small molecular weight drugs in radiation-crosslinked poly(ethylene oxide) hydrogels," Journal of Controlled Release 42 (1996) 195-202.
E. G. Rippie et al., "Regulation of Dissolution Rate by Pellet Geometry," Journal of Pharmaceutical Sciences, Vo. 58, No. 4, Apr. 1969, pp. 428-431.
M. Adel El-Egakey et al., "Hot extruded dosage forms Part I," Pharmaceutica Acta Helvetiae, vol. 46, Mar. 19, 1970.
Remington's Pharmaceutical Sciences 17th ed., Mack Publishing Co., (1985) 1418.
M.S. Mesiha et al., "A Screening Study of Lubricants in Wet Powder Masses Suitable for Extrusion Spheronization," Drug Development and Industrial Pharmacy, 19(8), 943-959 (1993).
N. Follonier et al., "Evaluation of Hot-Melt Extrusion as a New Technique for the Production of Polymer-Based Pellets for Sustained Release Capsules Containing High Loadings of Freely Soluble Drugs," Drug Development and Industrial Pharmacy, 20(8), 1323-1339 (1994).
Remington's Pharmaceutical Sciences, Authur Asol editor, pp. 1553-1593, Chapter 89, 1980.
Inert Gas from Wikipedia (Dec. 2009).
Coppens et al; "Hypromellose, Ethylcellulose, and Polyethylene Oxide Use in Hot Melt Extrusion"; Pharmaceutical Technology, 62-70, Jan. 2005.
Caraballo et al., "Percolation Thresholds in Ultrasound Compacted Tablets", Journal of Controlled Release, vol. 69, pp. 345-355, (2000).
El-Sherbiny et al., "Preparation Characterization, Swelling and in Vitro Drug Release Behaviour of Poly[N-acryloylglycine-chitosan] Interpolymeric pH and Thermally-responsice Hydrogels", European Polymer Journal, vol. 41, pp. 2584-2591 (2005).
Griffith R., "Tablet Crushing and the Law: The Implications for Nursing", Drug Administration, vol. 19, No. 1, p. 41-42 (2003).
Levina et al., "The Effect of Ultrasonic Vibration on the Compaction Characteristic of Paracetamol", Journal of Pharmaceutical Sciences, vol. 89, No. 6, pp. 705-723, Jun. 2000.
Levina et al., "The Effecto of Ultrasonic Vibration on the Compaction Characteristic of Ibuprofen", Drug Development and Industrial Pharmacy, vol. 28, No. 5, pp. 495-514 (2002).
Miller, et al., "To Crush or Not to Be Crush", Nursing, p. 50-52, Feb. 2000.
Mitchell J.E., "Oral Dosage Forms That Should Not Be Crushed: 2000 Update", Special Resource, vol. 35, No. 5, pp. 553-557, (2000).
Proeschel et al., "Task-Dependence of Activity/Bite-force Relations and its Impact on Estimation of Chewing Force from EMG", J. Dent. Res., vol. 81, No. 7, pp. 464-468 (2002).
Jan. 6, 2011 Letter from Dr. Rick Matos, Ph.D.
Seach result conducted on http://www.unitconversion.org/force/newtons-to-kiloponds-conversion.html on Jul. 5, 2011.
Katz et al., Clin. J. Pain, 23(8): 648-660 (2007).
Arnold, "Teen Abuse of Painkiller OxyContin on the Rise," www.npr.org, Dec. 19, 2005.
Baum et al., Public Health Reports, 102(4): 426-429 (1987).
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002.
Strang, British Med. J., 302: 969 (1991).
Tompkins et al., Psychopharma., 210: 471-480 (2010).
Waters et al., Am. J. Psychiatry, 164(1): pp. 173-174 (2007).
Tablet, www.docstoc.com (2011).
Dachille, F. et al., "High-Pressure Phase Transformation in Laboratory Mechanical Mixers and Mortars", 1906., Nature, 186, pp. 1-2 (abstract).
Yarbrough et al., Letters to Nature 322, 347-349 (Jul. 24, 1986) "Extraodinary effects of mortar-and-pestle grinding on microstructure of sintered alumina gel".
Braun, et al. Angel Orthodontist, 6(5) pp. 373-377, 1995.
Dow Excipients Chem. of Poly. Water Soluble Resin 2004.
Davis et al., European Journal of Pharmaceutics and Biopharmaceutics, 67, 2007, pp. 268-276.
Fell, et al. Journal of Pharmaceutical Sciences, vol. 59, No. 5, May 1970, pp. 688-691.
Lockhart et al. "Packaging of Pharmaceuticals and Health Care Products"; Blackie Academic & Professional; First Edition 1996.
Manthena et al., Amer J Drug Deliv. 2004: 2(1): 43-57.
Summers et al; Journal of Pharmaceutical Sciences, vol. 66, No. 8, Aug. 1977, pp. 1172-1175.
Tipler et al. Physics for Scientists and Engineers, 6th Edition, pp. 234-235, 2003.
US Pharmacopoeia, Chapter 1217, Aug. 1, 2008.
Waltimo et al. A novel bite force recorder and maximal isometric bite force values for healthy young adults. Scand J Dent Res. 1993, vol. 101, pp. 171-175.
Waltimo et al. Maximal bite force and its association with signs and symptoms of crandiomandibular disorders in young Finnish non-patients. Acta Odonol. Scand. 1995, vol. 53, pp. 254-258.
Conversion of 18.8 kiloponds to newtons, http://www.unitconversion.org/force/newtons-to-kiloponds-conversion.html on Jul. 5, 2011.
Bauer, Coated Pharmaceutical Dosage Forms, CRC Press, 1998, pp. 1-10.
Dachille, T., et al. "High-pressure phase transformation in laboratory mechanical mixers and mortars", 1960, Nature, 186, pp. 1-2 (abstract).
Maggi, L. et al., "High molecular weight polyethylene oxides (PEOs) as an alternative to HPMC in controlled release dosage form", 2000, International Journal of Pharmaceutics, 195 pp, 229-238.
Maggi, "Therapeutic Potential of Capsaicin-like Molecules: Studies in Animals and Humans", Life Sciences, vol. 51, pp. 1777-1781, (1992).
2.9 Methoden der pharmazeutischen Technologie, pp. 143-144, 1997 (English Translation included).
Handbuch der Kunststoff-Extrusionstechnik, "Grundlagen", Chapter 1.2 "Klassifizierung von Extrudern", pp. 3-7, 1989, (English Translation included).

Freed et al. pH control of nucleophilic/electrophilic oxidation. International Journal of Pharmaceutics. 2008, vol. 357, pp. 180-188.

Waterman et al. Stabilization of Pharmaceuticals to Oxidative Degradation. Pharmaceutical Development and Technology. 2002, vol. 7, No. 1, pp. 1-32.

J. Stafford, "Überzogene feste Formen", H. Sucker, Georg Thieme Verlag 1991, pp. 347-368.

"Pharmaceutical technical procedures", European Pharmacopofia, 1997, p. 135.

Granulierung hydrophober Wirkstoffe im Planetwalzenextruder 2003.

Pharmazeutische Biologie Drogen und ihre Inhaltsstoffe, Professor Dr. Hildebert Wagner, Munchen, 1982, pp. 82-92.

Coated Pharmaceutical Dosage Forms, K.H. Bauer, et al., CRC Press, 1998, pp. 1-10.

\* cited by examiner

ABUSE-PROOFED DOSAGE FORM

BACKGROUND OF THE INVENTION

1. Field of the Invention

The present invention relates to an abuse-proofed, thermoformed dosage form containing, in addition to one or more active ingredients with abuse potential (A) optionally together with physiologically acceptable auxiliary substances (B), at least one synthetic or natural polymer (C) and optionally at least one wax (D), wherein component (C) exhibits a breaking strength of at least 500 N, and to a process for the production of the dosage form according to the invention.

2. Brief Description of Related Developments

Many pharmaceutical active ingredients, in addition to having excellent activity in their appropriate application, also have abuse potential, i.e. they can be used by an abuser to bring about effects other than those intended. Opiates, for example, which are highly active in combating severe to very severe pain, are frequently used by abusers to induce a state of narcosis or euphoria.

In order to make abuse possible, the corresponding dosage forms, such as tablets or capsules are comminuted, for example ground in a mortar, by the abuser, the active ingredient is extracted from the resultant powder using a preferably aqueous liquid and the resultant solution, optionally after being filtered through cotton wool or cellulose wadding, is administered parenterally, in particular intravenously. An additional phenomenon of this kind of administration, in comparison with abusive oral administration, is a further accelerated increase in active ingredient levels giving the abuser the desired effect, namely the "kick" or "rush". This kick is also obtained if the powdered dosage form is administered nasally, i.e. is sniffed. Since controlled-release dosage forms containing active ingredients with abuse potential do not give rise to the kick desired by the abuser when taken orally even in abusively high quantities, such dosage forms are also comminuted and extracted in order to be abused.

U.S. Pat. No. 4,070,494 proposed adding a swellable agent to the dosage form in order to prevent abuse. When water is added to extract the active ingredient, this agent swells and ensures that the filtrate separated from the gel contains only a small quantity of active ingredient.

The multilayer tablet disclosed in WO 95/20947 is based on a similar approach to preventing parenteral abuse, said tablet containing the active ingredient with abuse potential and at least one gel former, each in different layers.

WO 03/015531 A2 discloses another approach to preventing parenteral abuse. A dosage form containing an analgesic opioid and a dye as an aversive agent is described therein. The colour released by tampering with the dosage form is intended to discourage the abuser from using the dosage form which has been tampered with.

Another known option for complicating abuse involves adding antagonists to the active ingredients to the dosage form, for example naloxone or naltexone in the case of opiates, or compounds which cause a physiological defence response, such as for example Radix ipecacuanha=ipecac root.

SUMMARY OF THE INVENTION

However, since in most cases of abuse it is still necessary to pulverise the dosage form comprising an active ingredient suitable for abuse, it was the object of the present invention to complicate or prevent the pulverisation preceding abuse of the dosage form comprising the agents conventionally available for potential abuse and accordingly to provide a dosage form for active ingredients with abuse potential which ensures the desired therapeutic effect when correctly administered, but from which the active ingredients cannot be converted into a form suitable for abuse simply by pulverisation.

Said object has been achieved by the provision of the abuse-proofed, thermoformed dosage form according to the invention which contains, in addition to one or more active ingredients with abuse potential (A), at least one synthetic or natural polymer (C) and optionally at least one wax (D), wherein component (C) exhibits a breaking strength of at least 500 N.

The use of polymers having the stated minimum breaking strength, preferably in quantities such that the dosage form also exhibits such a minimum breaking strength, means that pulverisation of the dosage form is considerably more difficult using conventional means, so considerably complicating or preventing the subsequent abuse.

If comminution is inadequate, parenteral, in particular intravenous, administration cannot be performed safely or extraction of the active ingredient therefrom takes too long for the abuser or there is no "kick" when taken orally, as release is not spontaneous.

According to the invention, comminution is taken to mean pulverisation of the dosage form with conventional means which are available to an abuser, such as for example a mortar and pestle, a hammer, a mallet or other usual means for pulverisation by application of force.

The dosage form according to the invention is thus suitable for preventing parenteral, nasal and/or oral abuse of pharmaceutical active ingredients with abuse potential.

Pharmaceutical active ingredients with abuse potential are known to the person skilled in the art, as are the quantities thereof to be used and processes for the production thereof, and may be present in the dosage form according to the invention as such, in the form of the corresponding derivatives thereof, in particular esters or ethers, or in each case in the form of corresponding physiologically acceptable compounds, in particular in the form of the salts or solvates thereof, as racemates or stereoisomers. The dosage form according to the invention is also suitable for the administration of several active ingredients. It is preferably used to administer a specific active ingredient.

The dosage form according to the invention is in particular suitable for preventing abuse of a pharmaceutical active ingredient selected from the group consisting of opiates, opioids, tranquillisers, preferably benzodiazepines, barbiturates, stimulants and other narcotics.

The dosage form according to the invention is very particularly suitable for preventing abuse of an opiate, opioid, tranquilliser or another narcotic selected from the group consisting of N-{1-[2-(4-ethyl-5-oxo-2-tetrazolin-1-yl)ethyl]-4-methoxymethyl-4-piperidyl}propionanilide (alfentanil), 5,5-diallylbarbituric acid (allobarbital), allylprodine, alphaprodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methyl-phenethylamine (amphetamine), 2-α-methylphenethylamino)-2-phenylacetonitrile (amphetaminil), 5-ethyl-5-isopentylbarbituric acid (amobarbital), anileridine, apocodeine, 5,5-diethylbarbituric acid (barbital), benzylmorphine, bezitramide, 7-bromo-5-(2-pyridyl)-1H-1,4-benzodiazepine-2(3H)-one (bromazepam), 2-bromo-4-(2-chlorophenyl)-9-methyl-6H-thieno[3,2-f][1,2,4]triazolo-[4,3-a][1,4]diazepine (brotizolam), 17-cyclopropylmethyl-4,5α-epoxy-7α[(S)-1-hydroxy-1,2,2-trimethyl-propyl]-6- methoxy-6,14-endo-ethanomorphinane-3-ol (buprenorphine), 5-butyl-5-ethylbarbituric acid (butobarbital), butorphanol, (7-chloro-1,3-dihydro-1-methyl-2-oxo-5-phenyl-2H-1,4-benzodiazepine-3-yl)-dimethylcarbamate (camazepam), (1S,2S)-2-amino-1-phenyl-1-propanol (cathine/D-norpseudoephedrine), 7-chloro-N-methyl-5-phenyl-3H-1,4-benzodiazepine-2-ylamine-4-oxide (chlorodiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepine-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepine-2(3H)-one (clotiazepam), 10-chloro-11b-(2-chlorophenyl)-2,3,7,11b-tetrahydrooxazolo[3,2-d][1,4]benzodiazepine-6(5H)-one (cloxazolam), (−)-methyl-[3β-benzoyloxy-2β(1α(H,5αH)-tropancarboxylate] (cocaine), 4,5α-epoxy-3-methoxy-17-methyl-7-morphinene-6α-ol (codeine), 5-(1-cyclohexenyl)-5-ethylbarbituric acid (cyclobarbital), cyclorphan, cyprenorphine, 7-chloro-5-(2-chlorophenyl)-1H-1,4-benzodiazepine-2(3H)-one (delorazepam), desomorphine, dextromoramide, (+)-(1-benzyl-3-dimethylamino-2-methyl-1-phenylpropyl)propionate (dextropropoxyphen), dezocine, diampromide, diamorphone, 7-chloro-1-methyl-5-phenyl-1H-1,4-benzodiazepine-2(3H)-one (diazepam), 4,5α-epoxy-3-methoxy-17-methyl-6α-morphinanol (dihydrocodeine), 4,5α-epoxy-17-methyl-3,6α-morphinandiol (dihydromorphine), dimenoxadol, dimepheptanol, dimethylthiambutene, dioxaphetyl butyrate, dipipanone, (6aR,10aR)-6,6,9-trimethyl-3-pentyl-6a,7,8,10a-tetrahydro-6H-benzo[c]chromene-1-ol (dronabinol), eptazocine, 8-chloro-6-phenyl-4H-[1,2,4]triazolo[4,3-a][1,4]benzodiazepine (estazolam), ethoheptazine, ethylmethylthiambutene, ethyl [7-chloro-5-(2-fluorophenyl)-2,3-dihydro-2-oxo-1H-1,4-benzodiazepine-3-carboxylate](ethyl loflazepate), 4,5α-epoxy-3-ethoxy-17-methyl-7-morphinene-6α-ol (ethylmorphine), etonitazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine (fencamfamine), 7-[2-(1-methyl-phenethylamino)ethyl]-theophylline) (fenethylline), 3-(α-methylphenethylamino)propionitrile (fenproporex), N-(1-phenethyl-4-piperidyl)propionanilide (fentanyl), 7-chloro-5-(2-fluorophenyl)-1-methyl-1H-1,4-benzodiazepine-2(3H)-one (fludiazepam), 5-(2-fluorophenyl)-1-methyl-7-nitro-1H-1,4-benzodiazepine-2(3H)-one (flunitrazepam), 7-chloro-1-(2-diethylaminoethyl)-5-(2-fluorophenyl)-1H-1,4-benzodiazepine-2(3H)-one (flurazepam), 7-chloro-5-phenyl-1-(2,2,2-trifluoroethyl)-1H-1,4-benzodiazepine-2(3H)-one (halazepam), 10-bromo-11b-(2-fluorophenyl)-2,3,7,11b-tetrahydro[1,3]oxazolyl[3,2-d][1,4]benzodiazepine-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethyl morphinane, 11-chloro-8,12b-dihydro-2,8-dimethyl-12b-phenyl-4H-[1,3]oxazino[3,2-d][1,4]benzodiazepine-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenyl-heptan-3-yl acetate (levacetylmethadol (LAAM)), (−)-6-dimethyl-amino-4,4-diphenol-3-heptanone (levomethadone), (−)-17-methyl-3-morphinanol (levorphanol), levophenacylmorphane, lofentanil, 6-(2-chlorophenyl)-2-(4-methyl-1-piperazinylmethylene)-8-nitro-2H-imidazo[1,2-a][1,4]-benzodiazepine-1(4H)-one (loprazolam), 7-chloro-5-(2-chlorophenyl)-3-hydroxy-1H-1,4-benzodiazepine-2(3H)-one (lorazepam), 7-chloro-5-(2-chlorophenyl)-3-hydroxy-1-methyl-1H-1,4-benzodiazepine-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenethylamine (mefenorex), meperidine, 2-methyl-2-propyltrimethylene dicarbamate (meprobamate), meptazinol, metazocine, methylmorphine, N,α-dimethylphenethylamine (methamphetamine), (±)-6-dimethylamino-4,4-diphenyl-3-heptanone (methadone), 2-methyl-3-o-tolyl-4(3H)-quinazolinone (methaqualone), methyl [2-phenyl-2-(2-piperidyl)acetate](methylphenidate), 5-ethyl-1-methyl-5-phenylbarbituric acid (methylphenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsulfinyl)-acetamide (modafinil), 4,5α-epoxy-17-methyl-7-morphinen-3,6α-diol (morphine), myrophine, (±)-trans-3-(1,1-dimethylheptyl)-7,8,10,10α-tetrahydro-1-hydroxy-6,6-dimethyl-6H-dibenzo[b,d]pyrane-9 (6αH)-one (nabilone), nalbuphine, nalorphine, narceine, nicomorphine, 1-methyl-7-nitro-5-phenyl-1H-1,4-benzodiazepine-2(3H)-one (nimetazepam), 7-nitro-5-phenyl-1H-1,4-benzodiazepine-2(3H)-one (nitrazepam), 7-chloro-5-phenyl-1H-1,4-benzodiazepine-2(3H)-one (nordazepam), norlevorphanol, 6-dimethylamino-4,4-diphenyl-3-hexanone (normethadone), normorphine, norpipanone, the exudation of plants belonging to the species *Papaver somniferum* (opium), 7-chloro-3-hydroxy-5-phenyl-1H-1,4-benzodiazepine-2(3H)-one (oxazepam), (cis-trans)-10-chloro-2,3,7,11b-tetrahydro-2-methyl-11b-phenyloxazolo[3,2-d][1,4]benzodiazepine-6-(5H)-one (oxazolam), 4,5α-epoxy-14-hydroxy-3-methoxy-17-methyl-6-morphinanone (oxycodone), oxymorphone, plants and parts of plants belonging to the species *Papaver somniferum* (including the subspecies *setigerum*), papaveretum, 2-imino-5-phenyl-4-oxazolidinone (pernoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)-barbituric acid (pentobarbital), ethyl-(1-methyl-4-phenyl-4-piperidine carboxylate) (pethidine), phenadoxone, phenomorphan, phenazocine, phenoperidine, piminodine, pholcodine, 3-methyl-2-phenylmorpholine (phenmetrazine), 5-ethyl-5-phenylbarbituric acid (phenobarbital), α,α-dimethylphenethylamine (phentermine), 7-chloro-5-phenyl-1-(2-propynyl)-1H-1,4-benzodiazepine-2(3H)-one (pinazepam), α-(2-piperidyl)benzhydryl alcohol (pipradrol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepine-2(3H)-one (prazepam), profadol, proheptazine, promedol, properidine, propoxyphene, N-(1-methyl-2-piperidinoethyl)-N-(2-pyridyl)propionamide, methyl {3-[4-methoxycarbonyl-4-(N-phenylpropanamido)piperidino]propanoate} (remifentanil), 5-sec-butyl-5-ethylbarbituric acid (secbutabarbital), 5-allyl-5-(1-methylbutyl)-barbituric acid (secobarbital), N-{4-methoxymethyl-1-[2-(2-thienyl)ethyl]-4-piperidyl}-propionanilide (sufentanil), 7-chloro-2-hydroxy-methyl-5-phenyl-1H-1,4-benzodiazepin-2(3H)-one (temazepam), 7-chloro-5-(1-cyclohexenyl)-1-methyl-1H-1,4-benzodiazepine-2(3H)-one (tetrazepam), ethyl(2-dimethylamino-1-phenyl-3-cyclohexene-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinylbarbituric acid (vinylbital), (1R*,2R*)-3-(3-dimethylamino-1-ethyl-2-methyl-propyl)-phenol, (1R,2R,4S)-2-(dimethylamino)methyl-4-(p-fluoro-benzyloxy)-1-(m-methoxyphenyl)cyclohexanol, (1R,2R)-3-(2- dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, 3-(2-dimethylaminomethyl-1-hydroxy-cyclohexyl)phenyl 2-(4-isobutoxy-phenyl)-propionate, 3-(2-dimethylaminomethyl-1-hydroxy-cyclohexyl) phenyl 2-(6-methoxy-naphthalen-2-yl)-propionate, 3-(2-dimethylamino-methyl-cyclohex-1-enyl)-phenyl 2-(4-isobutyl-phenyl)-propionate, 3-(2-dimethylaminomethyl-cyclohex-1-enyl)-phenyl 2-(6-methoxy-naphthalen-2-yl)-propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxy-benzoic acid 3-(2-dimethylaminomethyl-1-hydroxy-cyclohexyl)-phenyl ester, (RR—SS)-2-hydroxy-4-methyl-benzoic acid 3-(2-dimethylamino-methyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester and for corresponding stereoisomeric compounds, the corresponding derivatives thereof in each case, in particular esters or ethers, and the physiologically acceptable compounds thereof in each case, in particular the salts and solvates thereof.

The compounds (1R*,2R*)-3-(3-dimethylamino-1-ethyl-2-methyl-propyl)-phenol, (1R,2R,4S)-2-(dimethylamino)methyl-4-(p-fluorobenzyloxy)-1-(m-methoxyphenyl)cyclohexanol or the stereoisomeric compounds thereof or the physiologically acceptable compounds thereof, in particular the hydrochlorides thereof, the derivatives thereof, such as esters or ethers, and processes for the production thereof are known, for example, from EP-A-693475 or EP-A-780369. The corresponding descriptions are hereby introduced as a reference and are deemed to be part of the disclosure.

In order to achieve the necessary breaking strength of the dosage form according to the invention, at least one synthetic or natural polymer (C) is used which has a breaking strength, measured using the method disclosed in the present application, of at least 500 N. At least one polymer selected from the group consisting of polymethylene oxide, polyethylene oxide, polypropylene oxide, polyethylene, polypropylene, polyvinyl chloride, polycarbonate, polystyrene, polyacrylate, copolymers thereof, and mixtures of at least two of the stated polymers is preferably used for this purpose. The polymers are distinguished by a molecular weight of at least 0.5 million, determined by rheological measurements. In one embodiment, the molecular weight ranges from 1-15 million. Thermoplastic polyalkylene oxides, such as polyethylene oxides, with a molecular weight of at least 0.5 million, preferably of up to 15 million, determined by rheological measurements, are very particularly preferred. These polymers have a viscosity at 25° C. of 4500 to 17600 cP, measured on a 5 wt. % aqueous solution using a model RVF Brookfield viscosimeter (spindle no. 2/rotational speed 2 rpm), of 400 to 4000 cP, measured on a 2 wt. % aqueous solution using the stated viscosimeter (spindle no. 1 or 3/rotational speed 10 rpm) or of 1650 to 10000 cP, measured on a 1 wt. % aqueous solution using the stated viscosimeter (spindle no. 2/rotational speed 2 rpm).

The polymers are used in powder form.

In order to achieve the necessary breaking strength of the dosage form according to the invention, it is furthermore possible additionally to use at least one natural or synthetic wax (D) with a breaking strength, measured using the method disclosed in the present application, of at least 500 N. Waxes with a softening point of at least 60° C. are preferred. Carnauba wax and beeswax are particularly preferred. Carnauba wax is very particularly preferred. Carnauba wax is a natural wax which is obtained from the leaves of the carnauba palm and has a softening point of ≧80° C. When the wax component is additionally used, it is used together with at least one polymer (C) in quantities such that the dosage form has a breaking strength of at least 500 N.

The dosage forms according to the invention are distinguished in that, due their hardness, they cannot be pulverised, for example by grinding in a mortar. This virtually rules out oral or parenteral, in particular intravenous or nasal abuse. However, in order to prevent any possible abuse in the event of comminution and/or pulverisation of the dosage form according to the invention which has nevertheless been achieved by application of extreme force, the dosage forms according to the invention may, in a preferred embodiment, contain further agents which complicate or prevent abuse as auxiliary substances (B).

The abuse-proofed dosage form according to the invention, which comprises, apart from one or more active ingredients with abuse potential, at least one hardening polymer (C) and optionally at least one wax (D), may accordingly also comprise at least one of the following components (a)-(f) as auxiliary substances (B):

(a) at least one substance which irritates the nasal passages and/or pharynx,
(b) at least one viscosity-increasing agent, which, with the assistance of a necessary minimum quantity of an aqueous liquid, forms a gel with the extract obtained from the dosage form, which gel preferably remains visually distinguishable when introduced into a further quantity of an aqueous liquid,
(c) at least one antagonist for each of the active ingredients with abuse potential,
(d) at least one emetic,
(e) at least one dye as an aversive agent,
(f) at least one bitter substance.

Components (a) to (f) are additionally each individually suitable for abuse-proofing the dosage form according to the invention. Accordingly, component (a) is preferably suitable for proofing the dosage form against nasal, oral and/or parenteral, preferably intravenous, abuse, component (b) is preferably suitable for proofing against parenteral, particularly preferably intravenous and/or nasal abuse, component (c) is preferably suitable for proofing against nasal and/or parenteral, particularly preferably intravenous, abuse, component (d) is preferably suitable for proofing against parenteral, particularly preferably intravenous, and/or oral and/or nasal abuse, component (e) is suitable as a visual deterrent against oral or parenteral abuse and component (f) is suitable for proofing against oral or nasal abuse. Combined use according to the invention of at least one of the above-stated components makes it possible still more effectively to prevent abuse of dosage forms according to the invention.

In one embodiment, the dosage form according to the invention may also comprise two or more of components (a)-(f) in a combination, preferably (a), (b) and optionally (c) and/or (f) and/or (e) or (a), (b) and optionally (d) and/or (f) and/or (e).

In another embodiment, the dosage form according to the invention may comprise all of components (a)-(f).

If the dosage form according to the invention comprises component (a) to counter abuse, substances which irritate the nasal passages and/or pharynx which may be considered according to the invention are any substances which, when administered via the nasal passages and/or pharynx, bring about a physical reaction which is either so unpleasant for the abuser that he/she does not wish to or cannot continue administration, for example burning, or physiologically counteracts taking of the corresponding active ingredient, for example due to increased nasal secretion or sneezing. These substances which conventionally irritate the nasal passages and/or pharynx may also bring about a very unpleasant sensation or even unbearable pain when administered parenterally, in particular intravenously, such that the abuser does not wish to or cannot continue taking the substance.

Particularly suitable substances which irritate the nasal passages and/or pharynx are those which cause burning, itching, an urge to sneeze, increased formation of secretions or a combination of at least two of these stimuli. Appropriate substances and the quantities thereof which are conventionally to be used are known per se to the skilled person or may be identified by simple preliminary testing.

The substance which irritates the nasal passages and/or pharynx of component (a) is preferably based on one or more constituents or one or more plant parts of at least one hot substance drug.

Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The dosage form according to the invention may preferably contain the plant parts of the corresponding hot substance drugs in a quantity of 0.01 to 30 wt. %, particularly preferably of 0.1 to 0.5 wt. %, in each case relative to the total weight dosage unit.

If one or more constituents of corresponding hot substance drugs are used, the quantity thereof in a dosage unit according to the invention preferably amounts to 0.001 to 0.005 wt. %, relative to the total weight of the dosage unit.

A dosage unit is taken to mean a separate or separable administration unit, such as for example a tablet or a capsule.

One or more constituents of at least one hot substance drug selected from the group consisting of Allii sativi bulbus (garlic), Asari rhizoma cum herba (*Asarum* root and leaves), Calami rhizoma (*calamus* root), Capsici fructus (*capsicum*), Capsici fructus acer (cayenne pepper), Curcumae longae rhizoma (turmeric root), Curcumae xanthorrhizae rhizoma (Javanese turmeric root), Galangae rhizoma (galangal root), Myristicae semen (nutmeg), *Piperis* nigri fructus (pepper), *Sinapis albae* semen (white mustard seed), *Sinapis* nigri semen (black mustard seed), Zedoariae rhizoma (zedoary root) and Zingiberis rhizoma (ginger root), particularly preferably from the group consisting of Capsici fructus (*capsicum*), Capsici fructus acer (cayenne pepper) and *Piperis* nigri fructus (pepper) may preferably be added as component (a) to the dosage form according to the invention.

The constituents of the hot substance drugs preferably comprise o-methoxy(methyl)phenol compounds, acid amide compounds, mustard oils or sulfide compounds or compounds derived therefrom.

Particularly preferably, at least one constituent of the hot substance drugs is selected from the group consisting of myristicin, elemicin, isoeugenol, β-asarone, safrole, gingerols, xanthorrhizol, capsaicinoids, preferably capsaicin, capsaicin derivatives, such as N-vanillyl-9E-octadecenamide, dihydrocapsaicin, nordihydrocapsaicin, homocapsaicin, norcapsaicin and nomorcapsaicin, piperine, preferably trans-piperine, glucosinolates, preferably based on non-volatile mustard oils, particularly preferably based on p-hydroxybenzyl mustard oil, methylmercapto mustard oil or methylsulfonyl mustard oil, and compounds derived from these constituents.

Another option for preventing abuse of the dosage form according to the invention consists in adding at least one viscosity-increasing agent as a further abuse-preventing component (b) to the dosage form, which, with the assistance of a necessary minimum quantity of an aqueous liquid, forms a gel with the extract obtained from the dosage form, which gel is virtually impossible to administer safely and preferably remains visually distinguishable when introduced into a further quantity of an aqueous liquid.

For the purposes of the present invention visually distinguishable means that the active ingredient-containing gel formed with the assistance of a necessary minimum quantity of aqueous liquid, when introduced, preferably with the assistance of a hypodermic needle, into a further quantity of aqueous liquid at 37° C., remains substantially insoluble and cohesive and cannot straightforwardly be dispersed in such a manner that it can safely be administered parenterally, in particular intravenously. The material preferably remains visually distinguishable for at least one minute, preferably for at least 10 minutes.

The increased viscosity of the extract makes it more difficult or even impossible for it to be passed through a needle or injected. If the gel remains visually distinguishable, this means that the gel obtained on introduction into a further quantity of aqueous liquid, for example by injection into blood, initially remains in the form of a largely cohesive thread, which, while it may indeed be broken up into smaller fragments, cannot be dispersed or even dissolved in such a manner that it can safely be administered parenterally, in particular intravenously. In combination with at least one optionally present component (a) to (e), this additionally leads to unpleasant burning, vomiting, bad flavour and/or visual deterrence.

Intravenous administration of such a gel would most probably result in obstruction of blood vessels, associated with serious embolism or even death of the abuser.

In order to verify whether a viscosity-increasing agent is suitable as component (b) for use in the dosage form according to the invention, the active ingredient is mixed with the viscosity-increasing agent and suspended in 10 ml of water at a temperature of 25° C. If this results in the formation of a gel which fulfils the above-stated conditions, the corresponding viscosity-increasing agent is suitable for preventing or averting abuse of the dosage forms according to the invention.

If component (b) is added to the dosage form according to the invention, one or more viscosity-increasing agents are used which are selected from the group consisting of microcrystalline cellulose with 11 wt. % carboxymethylcellulose sodium (Avicel® RC 591), carboxymethylcellulose sodium (Blanose®, CMC-Na C300P®, Frimulsion BLC-5®, Tylose C300 P®), polyacrylic acid (Carbopol® 980 NF, Carbopol® 981), locust bean flour (Cesagum® LA-200, Cesagum® LID/150, Cesagum® LN-1), pectins such as citrus pectin (Cesapectin® HM Medium Rapid Set), apple pectin, pectin from lemon peel, waxy maize starch (C*Gel 04201®), sodium alginate (Frimulsion ALG (E401)®), guar flour (Frimulsion BM®, Polygum 26/1-75®), iota carrageen (Frimulsion D021®), karaya gum, gellan gum (Kelcogel F®, Kelcogel LT100®), galactomannan (Meyprogat 150®), tara bean flour (Polygum 43/1), propylene glycol alginate (Protanal-Ester SD-LB®), sodium hyaluronate, tragacanth, tara gum (Vidogum SP 200®), fermented polysaccharide welan gum (K1A96), xanthan gum (Xantural 180®). Xanthans are particularly preferred. The names stated in brackets are the trade names by which the materials are known commercially. In general, a quantity of 0.1 to 5 wt. % of the viscosity-increasing agent(s) is sufficient to fulfil the above-stated conditions.

The component (b) viscosity-increasing agents, where provided, are preferably present in the dosage form according to the invention in quantities of ≧5 mg per dosage unit, i.e. per administration unit.

In a particularly preferred embodiment of the present invention, the viscosity-increasing agents used as component (b) are those which, on extraction from the dosage form with the necessary minimum quantity of aqueous liquid, form a gel which encloses air bubbles. The resultant gels are distinguished by a turbid appearance, which provides the potential abuser with an additional optical warning and discourages him/her from administering the gel parenterally.

It is also possible to formulate the viscosity-increasing agent and the other constituents in the dosage form according to the invention in a mutually spatially separated arrangement.

In order to discourage and prevent abuse, the dosage form according to the invention may furthermore comprise component (c), namely one or more antagonists for the active ingredient or active ingredients with abuse potential, wherein the antagonists are preferably spatially separated from the remaining constituents of the invention dosage according to the form and, when correctly used, do not exert any effect.

Suitable antagonists for preventing abuse of the active ingredients are known per se to the person skilled in the art and may be present in the dosage form according to the invention as such or in the form of corresponding derivatives, in particular esters or ethers, or in each case in the form of corresponding physiologically acceptable compounds, in particular in the form of the salts or solvates thereof.

If the active ingredient present in the dosage form is an opiate or an opioid, the antagonist used is preferably an antagonist selected from the group consisting of naloxone, naltrexone, nalmefene, nalid, nalmexone, nalorphine or naluphine, in each case optionally in the form of a corresponding physiologically acceptable compound, in particular in the form of a base, a salt or solvate. The corresponding antagonists, where component (c) is provided, are preferably used in a quantity of ≧10 mg, particularly preferably in a quantity of 10 to 100 mg, very particularly preferably in a quantity of 10 to 50 mg per dosage form, i.e. per administration unit.

If the dosage form according to the invention comprises a stimulant as active ingredient, the antagonist is preferably a neuroleptic, preferably at least one compound selected from the group consisting of haloperidol, promethazine, fluphenazine, perphenazine, levomepromazine, thioridazine, perazine, chlorpromazine, chlorprothixine, zuclopentixol, flupentixol, prothipendyl, zotepine, benperidol, pipamperone, melperone and bromperidol.

The dosage form according to the invention preferably comprises these antagonists in a conventional therapeutic dose known to the person skilled in the art, particularly preferably in a quantity of twice to four times the conventional dose per administration unit.

If the combination to discourage and prevent abuse of the dosage form according to the invention comprises component (d), it may comprise at least one emetic, which is preferably present in a spatially separated arrangement from the other components of the dosage form according to the invention and, when correctly used, is intended not to exert its effect in the body.

Suitable emetics for preventing abuse of an active ingredient are known per se to the person skilled in the art and may be present in the dosage form according to the invention as such or in the form of corresponding derivatives, in particular esters or ethers, or in each case in the form of corresponding physiologically acceptable compounds, in particular in the form of the salts or solvates thereof.

An emetic based on one or more constituents of radix ipecacuanha (ipecac root), preferably based on the constituent emetine may preferably be considered in the dosage form according to the invention, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, New York, 1982. The corresponding literature description is hereby introduced as a reference and is deemed to be part of the disclosure.

The dosage form according to the invention may preferably comprise the emetic emetine as component (d), preferably in a quantity of ≧10 mg, particularly preferably of ≧20 mg and very particularly preferably in a quantity of ≧40 mg per dosage form, i.e. administration unit.

Apomorphine may likewise preferably be used as an emetic in the abuse-proofing according to the invention, preferably in a quantity of preferably ≧3 mg, particularly preferably of ≧5 mg and very particularly preferably of ≧7 mg per administration unit.

If the dosage form according to the invention contains component (e) as a further abuse-preventing auxiliary substance, the use of a such a dye brings about an intense coloration of a corresponding aqueous solution, in particular when the attempt is made to extract the active ingredient for parenteral, preferably intravenous administration, which coloration may act as a deterrent to the potential abuser. Oral abuse, which conventionally begins by means of aqueous extraction of the active ingredient, may also be prevented by this coloration. Suitable dyes and the quantities required for the necessary deterrence may be found in WO 03/015531, wherein the corresponding disclosure should be deemed to be part of the present disclosure and is hereby introduced as a reference.

If the dosage form according to the invention contains component (f) as a further abuse-preventing auxiliary substance, this addition of at least one bitter substance and the consequent impairment of the flavour of the dosage form additionally prevents oral and/or nasal abuse.

Suitable bitter substances and the quantities effective for use may be found in US-2003/0064099 A1, the corresponding disclosure of which should be deemed to be the disclosure of the present application and is hereby introduced as a reference. Suitable bitter substances are preferably aromatic oils, preferably peppermint oil, eucalyptus oil, bitter almond oil, menthol, fruit aroma substances, preferably aroma substances from lemons, oranges, limes, grapefruit or mixtures thereof, and/or denatonium benzoate.

The solid dosage form according to the invention is suitable to be taken orally or rectally, preferably orally. The orally administrable dosage form according to the invention may assume multiparticulate form, preferably in the form of microtablets, microcapsules, micropellets, granules, spheroids, beads or pellets, optionally packaged in capsules or pressed into tablets. The multiparticulate forms preferably have a size or size distribution in the range from 0.1 to 3 mm, particularly preferably in the range from 0.5 to 2 mm.

Depending on the desired dosage form, conventional auxiliary substances (B) are optionally also used for the formulation of the dosage form.

The solid, abuse-proofed dosage form according to the invention is preferably produced by mixing the components (A), (B), (C) and/optionally (D) and at least one of the optionally present further abuse-preventing components (a)-(f) and, optionally after granulation, press-forming the resultant mixture to yield the dosage form with preceding, simultaneous, or subsequent exposure to heat.

Mixing of components (A), (B), (C) and optionally (D) and of the optionally present further components (a)-(f) proceeds in a mixer known to the person skilled in the art. The mixer may, for example, be a roll mixer, shaking mixer, shear mixer or compulsory mixer.

The resultant mixture is preferably formed directly by application of pressure to yield the dosage form according to the invention with preceding, simultaneous or subsequent exposure to heat. The mixture may, for example, be formed into tablets by direct tabletting. In direct tabletting with simultaneous exposure to heat, the tabletting tool, i.e. bottom punch, top punch and die are briefly heated at least to the softening temperature of the polymer (C) and pressed together. In direct tabletting with subsequent exposure to heat, the formed tablets are briefly heated at least to the softening temperature (glass transition temperature, melting temperature; sintering temperature) of component (C) and cooled again. In direct tabletting with preceding exposure to heat, the material to be pressed is heated immediately prior to tabletting at least to the softening temperature of component (C) and then pressed.

The resultant mixture of components (A), (B), (C) and optionally (D) and the optionally present components (a) to (f) may also first be granulated and then be formed with preceding, simultaneous, or subsequent exposure to heat to yield the dosage form according to the invention.

In a further preferred embodiment, the dosage form according to the invention assumes the form of a tablet, a capsule or is in the form of an oral osmotic therapeutic system (OROS), preferably if at least one further abuse-preventing component (a)-(f) is also present.

If components (c) and/or (d) and/or (f) are present in the dosage form according to the invention, care must be taken to ensure that they are formulated in such a manner or are present in such a low dose that, when correctly administered, the dosage form is able to bring about virtually no effect which impairs the patient or the efficacy of the active ingredient.

If the dosage form according to the invention contains component (d) and/or (f), the dosage must be selected such that, when correctly orally administered, no negative effect is caused. If, however, the intended dosage of the dosage form is exceeded inadvertently, in particular by children, or in the event of abuse, nausea or an inclination to vomit or a bad flavour are produced. The particular quantity of component (d) and/or (f) which can still be tolerated by the patient in the event of correct oral administration may be determined by the person skilled in the art by simple preliminary testing.

If, however, irrespective of the fact that the dosage form according to the invention is virtually impossible to pulverise, the dosage form containing the components (c) and/or (d) and/or (f) is provided with protection, these components should preferably be used at a dosage which is sufficiently high that, when abusively administered, they bring about an intense negative effect on the abuser. This is preferably achieved by spatial separation of at least the active ingredient or active ingredients from components (c) and/or (d) and/or (f), wherein the active ingredient or active ingredients is/are present in at least one subunit (X) and components (c) and/or (d) and/or (f) is/are present in at least one subunit (Y), and wherein, when the dosage form is correctly administered, components (c), (d) and (f) do not exert their effect on taking and/or in the body and the remaining components of the formulation, in particular component (C), are identical.

If the dosage form according to the invention comprises at least 2 of components (c) and (d) or (f), these may each be present in the same or different subunits (Y). Preferably, when present, all the components (c) and (d) and (f) are present in one and the same subunit (Y).

For the purposes of the present invention, subunits are solid formulations, which in each case, apart from conventional auxiliary substances known to the person skilled in the art, contain the active ingredient(s), at least one polymer (C) and optionally at least one of the optionally present components (a) and/or (b) and/or (e) or in each case at least one polymer (C) and the antagonist(s) and/or emetic(s) and/or component (e) and/or component (f) and optionally at least one of the optionally present components (a) and/or (b). Care must here be taken to ensure that each of the subunits is formulated in accordance with the above-stated process.

One substantial advantage of the separated formulation of active ingredients from components (c) or (d) or (f) in subunits (X) and (Y) of the dosage form according to the invention is that, when correctly administered, components (c) and/or (d) and/or (f) are hardly released on taking and/or in the body or are released in such small quantities that they exert no effect which impairs the patient or therapeutic success or, on passing through the patient's body, they are only liberated in locations where they cannot be sufficiently absorbed to be effective. When the dosage form is correctly administered, hardly any of components (c) and/or (d) and/or (f) is released into the patient's body or they go unnoticed by the patient.

The person skilled in the art will understand that the above-stated conditions may vary as a function of the particular components (c), (d) and/or (f) used and of the formulation of the subunits or the dosage form. The optimum formulation for the particular dosage form may be determined by simple preliminary testing. What is vital is that each subunit contains the polymer (C) and has been formulated in the stated manner.

Should, contrary to expectations, the abuser succeed in comminuting such a dosage form according to the invention, which comprises components (c) and/or (e) and/or (d) and/or (f) in subunits (Y), for the purpose of abusing the active ingredient and obtain a powder which is extracted with a suitable extracting agent, not only the active ingredient but also the particular component (c) and/or (e) and/or (f) and/or (d) will be obtained in a form in which it cannot readily be separated from the active ingredient, such that when the dosage form which has been tampered with is administered, in particular by oral and/or parenteral administration, it will exert its effect on taking and/or in the body combined with an additional negative effect on the abuser corresponding to component (c) and/or (d) and/or (f) or, when the attempt is made to extract the active ingredient, the coloration will act as a deterrent and so prevent abuse of the dosage form.

A dosage form according to the invention, in which the active ingredient or active ingredients is/are spatially separated from components (c), (d) and/or (e), preferably by formulation in different subunits, may be formulated in many different ways, wherein the corresponding subunits may each be present in the dosage form according to the invention in any desired spatial arrangement relative to one another, provided that the above-stated conditions for the release of components (c) and/or (d) are fulfilled.

The person skilled in the art will understand that component(s) (a) and/or (b) which are optionally also present may preferably be formulated in the dosage form according to the invention both in the particular subunits (X) and (Y) and in the form of independent subunits corresponding to subunits (X) and (Y), provided that neither the abuse-proofing nor the active ingredient release in the event of correct administration is impaired by the nature of the formulation and the polymer (C) is included in the formulation and formulation is carried out in accordance with the above-stated process.

In a preferred embodiment of the dosage form according to the invention, subunits (X) and (Y) are present in multiparticulate form, wherein microtablets, microcapsules, micropellets, granules, spheroids, beads or pellets are preferred and the same form, i.e. shape, is selected for both subunit (X) and subunit (Y), such that it is not possible to separate subunits (X) from (Y) by mechanical selection. The multiparticulate forms are preferably of a size in the range from 0.1 to 3 mm, preferably of 0.5 to 2 mm.

The subunits (X) and (Y) in multiparticulate form may also preferably be packaged in a capsule or be pressed into a tablet, wherein the final formulation in each case proceeds in such a manner that the subunits (X) and (Y) are also retained in the resultant dosage form.

The multiparticulate subunits (X) and (Y) of identical shape should also not be visually distinguishable from one another so that the abuser cannot separate them from one another by simple sorting. This may, for example, be achieved by the application of identical coatings which, apart from this disguising function, may also incorporate further functions, such as, for example, controlled release of one or more active ingredients or provision of a finish resistant to gastric juices on the particular subunits.

In a further preferred embodiment of the present invention, subunits (X) and (Y) are in each case arranged in layers relative to one another.

The layered subunits (X) and (Y) are preferably arranged for this purpose vertically or horizontally relative to one another in the dosage form according to the invention, wherein in each case one or more layered subunits (X) and one or more layered subunits (Y) may be present in the dosage form, such that, apart from the preferred layer sequences (X)-(Y) or (X)-(Y)-(X), any desired other layer sequences may be considered, optionally in combination with layers containing components (a) and/or (b).

Another preferred dosage form according to the invention is one in which subunit (Y) forms a core which is completely enclosed by subunit (X), wherein a separation layer (Z) may be present between said layers. Such a structure is preferably also suitable for the above-stated multiparticulate forms, wherein both subunits (X) and (Y) and an optionally present separation layer (Z), which must satisfy the hardness requirement according to the invention, are formulated in one and the same multiparticulate form. In a further preferred embodiment of the dosage form according to the invention, the subunit (X) forms a core, which is enclosed by subunit (Y), wherein the latter comprises at least one channel which leads from the core to the surface of the dosage form.

The dosage form according to the invention may comprise, between one layer of the subunit (X) and one layer of the subunit (Y), in each case one or more, preferably one, optionally swellable separation layer (Z) which serves to separate subunit (X) spatially from (Y).

If the dosage form according to the invention comprises the layered subunits (X) and (Y) and an optionally present separation layer (Z) in an at least partially vertical or horizontal arrangement, the dosage form preferably takes the form of a tablet, a coextrudate or a laminate.

In one particularly preferred embodiment, the entirety of the free surface of subunit (Y) and optionally at least part of the free surface of subunit(s) (X) and optionally at least part of the free surface of the optionally present separation layer(s) (Z) may be coated with at least one barrier layer (Z') which prevents release of component (c) and/or (e) and/or (d) and/or (f). The barrier layer (Z') must also fulfil the hardness conditions according to the invention.

Another particularly preferred embodiment of the dosage form according to the invention comprises a vertical or horizontal arrangement of the layers of subunits (X) and (Y) and at least one push layer (p) arranged therebetween, and optionally a separation layer (Z), in which dosage form the entirety of the free surface of layer structure consisting of subunits (X) and (Y), the push layer and the optionally present separation layer (Z) is provided with a semipermeable coating (E), which is permeable to a release medium, i.e. conventionally a physiological liquid, but substantially impermeable to the active ingredient and to component (c) and/or (d) and/or (f), and wherein this coating (E) comprises at least one opening for release of the active ingredient in the area of subunit (X).

A corresponding dosage form is known to the person skilled in the art, for example under the name oral osmotic therapeutic system (OROS), as are suitable materials and methods for the production thereof, inter alia from U.S. Pat. No. 4,612,008, U.S. Pat. No. 4,765,989 and U.S. Pat. No. 4,783,337. The corresponding descriptions are hereby introduced as a reference and are deemed to be part of the disclosure.

In a further preferred embodiment, the subunit (X) of the dosage form according to the invention is in the form of a tablet, the edge face of which and optionally one of the two main faces is covered with a barrier layer (Z') containing component (c) and/or (d) and/or (f).

The person skilled in the art will understand that the auxiliary substances of the subunit(s) (X) or (Y) and of the optionally present separation layer(s) (Z) and/or of the barrier layer(s) (Z') used in formulating the dosage form according to the invention will vary as a function of the arrangement thereof in the dosage form according to the invention, the mode of administration and as a function of the particular active ingredient of the optionally present components (a) and/or (b) and/or (e) and of component (c) and/or (d) and/or (f). The materials which have the requisite properties are in each case known per se to the person skilled in the art.

If release of component (c) and/or (d) and/or (f) from subunit (Y) of the dosage form according to the invention is prevented with the assistance of a cover, preferably a barrier layer, the subunit may consist of conventional materials known to the person skilled in the art, providing that it contains at least one polymer (C) to fulfil the hardness condition of the dosage form according to the invention.

If a corresponding barrier layer (Z') is not provided to prevent release of component (c) and/or (d) and/or (f), the materials of the subunits should be selected such that release of the particular component (c) and/or (d) from subunit (Y) is virtually ruled out. The materials which are stated below to be suitable for production of the barrier layer may preferably be used for this purpose. The materials for the separation layer and/or barrier layer must contain at least one polymer (C) in order to fulfil the hardness conditions.

Preferred materials are those which are selected from the group consisting of alkylcelluloses, hydroxyalkylcelluloses, glucans, scleroglucans, mannans, xanthans, copolymers of poly[bis(p-carboxyphenoxy)propane and sebacic acid, preferably in a molar ratio of 20:80 (commercially available under the name Polifeprosan 20®), carboxymethylcelluloses, cellulose ethers, cellulose esters, nitrocelluloses, polymers based on (meth)acrylic acid and the esters thereof, polyamides, polycarbonates, polyalkylenes, polyalkylene glycols, polyalkylene oxides, polyalkylene terephthalates, polyvinyl alcohols, polyvinyl ethers, polyvinyl esters, halogenated polyvinyls, polyglycolides, polysiloxanes and polyurethanes and the copolymers thereof.

Particularly suitable materials may be selected from the group consisting of methylcellulose, ethylcellulose, hydroxypropylcellulose, hydroxypropylmethylcellulose, hydroxybutylmethylcellulose, cellulose acetate, cellulose propionate (of low, medium or high molecular weight), cellulose acetate propionate, cellulose acetate butyrate, cellulose acetate phthalate, carboxymethylcellulose, cellulose triacetate, sodium cellulose sulfate, polymethyl methacrylate, polyethyl methacrylate, polybutyl methacrylate, polyisobutyl methacrylate, polyhexyl methacrylate, polyisodecyl methacrylate, polylauryl methacrylate, polyphenyl methacrylate, polymethyl acrylate, polyisopropyl acrylate, polyisobutyl acrylate, polyoctadecyl acrylate, polyethylene, low density polyethylene, high density polyethylene, polypropylene, polyethylene glycol, polyethylene oxide, polyethylene terephthalate, polyvinyl alcohol, polyvinyl isobutyl ether, polyvinyl acetate and polyvinyl chloride.

Particularly suitable copolymers may be selected from the group consisting of copolymers of butyl methacrylate and isobutyl methacrylate, copolymers of methyl vinyl ether and maleic acid with high molecular weight, copolymers of methyl vinyl ether and maleic acid monoethyl ester, copolymers of methyl vinyl ether and maleic anhydride and copolymers of vinyl alcohol and vinyl acetate.

Further materials which are particularly suitable for formulating the barrier layer are starch-filled polycaprolactone (WO98/20073), aliphatic polyesteramides (DE 19 753 534 A1, DE 19 800 698 A1, EP 0 820 698 A1), aliphatic and aromatic polyester urethanes (DE 19822979), polyhydroxyalkanoates, in particular polyhydroxybutyrates, polyhydroxyvalerates, casein (DE 4 309 528), polylactides and copolylactides (EP 0 980 894 A1). The corresponding descriptions are hereby introduced as a reference and are deemed to be part of the disclosure.

The above-stated materials may optionally be blended with further conventional auxiliary substances known to the person skilled in the art, preferably selected from the group consisting of glyceryl monostearate, semi-synthetic triglyceride derivatives, semi-synthetic glycerides, hydrogenated castor oil, glyceryl palmitostearate, glyceryl behenate, polyvinylpyrrolidone, gelatine, magnesium stearate, stearic acid, sodium stearate, talcum, sodium benzoate, boric acid and colloidal silica, fatty acids, substituted triglycerides, glycerides, polyoxyalkylene glycols and the derivatives thereof.

If the dosage form according to the invention comprises a separation layer (Z'), said layer, like the uncovered subunit (Y), may preferably consist of the above-stated materials described for the barrier layer. The person skilled in the art will understand that release of the active ingredient or of component (c) and/or (d) from the particular subunit may be controlled by the thickness of the separation layer.

The dosage form according to the invention may comprise one or more active ingredients at least partially in controlled release form, wherein controlled release may be achieved with the assistance of conventional materials and methods known to the person skilled in the art, for example by embedding the active ingredient in a controlled release matrix or by the application of one or more controlled release coatings. Active ingredient release must, however, be controlled such that the above-stated conditions are fulfilled in each case, for example that, in the event of correct administration of the dosage form, the active ingredient or active ingredients are virtually completely released before the optionally present component (c) and/or (d) can exert an impairing effect.

Controlled release from the dosage form according to the invention is preferably achieved by embedding the active ingredient in a matrix. The auxiliary substances acting as matrix materials control active ingredient release. Matrix materials may, for example, be hydrophilic, gel-forming materials, from which active ingredient release proceeds mainly by diffusion, or hydrophobic materials, from which active ingredient release proceeds mainly by diffusion from the pores in the matrix.

Physiologically acceptable, hydrophobic materials which are known to the person skilled in the art may be used as matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials.

Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of C12-C30 fatty acids and/or C12-C30 fatty alcohols and/or waxes or mixtures thereof are particularly preferably used as hydrophobic materials.

It is also possible to use mixtures of the above-stated hydrophilic and hydrophobic materials as matrix materials.

Component (C) and the optionally present component (D), which serve to achieve the breaking strength of at least 500 N which is necessary according to the invention may furthermore also optionally serve as additional matrix materials.

If the dosage form according to the invention is intended for oral administration, it may also preferably comprise a coating which is resistant to gastric juices and dissolves as a function of the pH value of the release environment. By means of this coating, it is possible to ensure that the dosage form according to the invention passes through the stomach undissolved and the active ingredient is only released in the intestines. The coating which is resistant to gastric juices preferably dissolves at a pH value of between 5 and 7.5.

Corresponding materials and methods for the controlled release of active ingredients and for the application of coatings which are resistant to gastric juices are known to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The corresponding literature description is hereby introduced as a reference and is deemed to be part of the disclosure.

Method for Determining Breaking Strength

A) In order to verify whether a polymer may be used as component (C), the polymer is pressed to form a tablet with a diameter of 10 mm and a height of 5 mm using a force of 150 N at a temperature which at least corresponds to the softening point of the polymer and is determined with the assistance of a DSC diagram of the polymer. Using tablets produced in this manner, breaking strength is determined with the apparatus described below in accordance with the method for determining the breaking strength of tablets published in the European Pharmacopoeia 1997, page 143-144, method no. 2.9.8. The apparatus used for the measurement is a series 3300 universal tester, single column benchtop model no. 3345 from Instron®, Canton, Mass., USA. The clamping tool used is a pressure piston with a diameter of 25 mm, which can be subjected to a load of up to 1 kN (item no. 2501-3 from Instron®).

An Instron® universal tester, single column benchtop model no. 5543, with the above-stated clamping tool may also be used to carry out the measurement.

The tablets deemed to be resistant to breaking under a specific load include not only those which have not broken but also those which may have suffered plastic deformation under the action of the force.

Providing that the dosage form is in tablet form, breaking strength may be determined using the same measurement method.

The following Examples illustrate the invention purely by way of example and without restricting the general concept of the invention.

EXAMPLES

Tramadol hydrochloride was used as the active ingredient in a series of Examples. Tramadol hydrochloride was used, despite tramadol not being an active ingredient which conventionally has abuse potential, because it is not governed by German narcotics legislation, so simplifying the experimental work. Tramadol is moreover a member of the opioid class with excellent water solubility.

Example 1

| Components | Per tablet | Complete batch |
|---|---|---|
| Tramadol hydrochloride | 100 mg | 100 g |
| Polyethylene oxide, NF, MFI (190° C. at 21.6 kg/10 min) <0.5 g MW 7 000 000 (Polyox WSR 303, Dow Chemicals) | 200 mg | 200 g |
| Total weight | 300 mg | 300 g |

Tramadol hydrochloride and polyethylene oxide powder were mixed in a free-fall mixer. A tabletting tool with top punch, bottom punch and die for tablets with a diameter of 10 mm and a radius of curvature of 8 mm was heated to 80° C. in a heating cabinet. 300 mg portions of the powder mixture were pressed with the heated tool, wherein pressure was maintained for at least 15 seconds by clamping the tabletting tool in a vice.

The breaking strength of the tablets was determined with the stated apparatus in accordance with the stated method. The tablets did not break when exposed to a force of 500 N. The tablet could not be comminuted using a hammer, nor with the assistance of a mortar and pestle.

In vitro release of the active ingredient from the preparation was determined in a paddle stirrer apparatus in accordance with Pharm. Eur. The temperature of the release medium was 37° C. and the rotational speed of the stirrer 75 $min^{-1}$. At the beginning of the investigation, each tablet was placed in a 600 ml portion of artificial gastric juice, pH 1.2. After 30 minutes, the pH value was increased to 2.3 by addition of alkali solution, after a further 90 minutes to pH 6.5 and after a further 60 minutes to pH 7.2. The released quantity of active ingredient present in the dissolution medium at each point in time was determined by spectrophotometry.

| Time | Released quantity |
|---|---|
| 30 min | 15% |
| 240 min | 52% |
| 480 min | 80% |
| 720 min | 99% |

Example 2

300 mg portions of the powder mixture from Example 1 were heated to 80° C. and in placed in the die of the tabletting tool. Pressing was then performed. The tablet exhibits the same properties such as the tablet in Example 1.

Example 3

| Raw material | Per tablet | Complete batch |
|---|---|---|
| Tramadol hydrochloride | 50 mg | 100 g |
| Polyethylene oxide, NF, MW 7 000 000 (Polyox WSR 303, Dow Chemicals) | 100 mg | 200 g |
| Total weight | 150 mg | 300 g |

Tramadol hydrochloride and the above-stated components were mixed in a free-fall mixer. A tabletting tool with top punch, bottom punch and die for tablets with a diameter of 7 mm was heated to 80° C. in a heating cabinet. 150 mg portions of the powder mixture were pressed with the heated tool, wherein pressure was maintained for at least 15 seconds by clamping the tabletting tool in a vice.

The breaking strength of the tablets was determined with the stated apparatus in accordance with the stated method. The tablets did not break when exposed to a force of 500 N.

In vitro release of the active ingredient was determined as in Example 1 and was:

| Time | Released quantity |
|---|---|
| 30 min | 15% |
| 240 min | 62% |
| 480 min | 88% |
| 720 min | 99% |

Example 4

| Raw material | Per tablet | Complete batch |
|---|---|---|
| Tramadol hydrochloride | 100 mg | 100 g |
| Polyethylene oxide, NF, MW 7 000 000 (Polyox WSR | 180 mg | 180 g |

| Raw material | Per tablet | Complete batch |
|---|---|---|
| 303, Dow Chemicals) | | |
| Xanthan, NF | 20 mg | 20 g |
| Total weight | 300 mg | 300 g |

Tramadol hydrochloride, xanthan and polyethylene oxide were mixed in a free-fall mixer. A tabletting tool with top punch, bottom punch and die for tablets with a diameter of 10 mm and a radius of curvature of 8 mm was heated to 80° C. in a heating cabinet. 300 mg portions of the powder mixture were pressed with the heated tool, wherein pressure was maintained for at least 15 seconds by clamping the tabletting tool in a vice.

The breaking strength of the tablets was determined with the stated apparatus in accordance with the stated method. The tablets did not break when exposed to a force of 500 N. The tablets did suffer a little plastic deformation.

In vitro release of the active ingredient was determined as in Example 1 and was:

| Time | Released quantity |
|---|---|
| 30 min | 14% |
| 240 min | 54% |
| 480 min | 81% |
| 720 min | 99% |

The tablets could be cut up with a knife into pieces of an edge length of as small as approx. 2 mm. No further comminution proceeding as far as pulverisation was possible. When the pieces are combined with water, a highly viscous gel is formed. Only with great difficulty could the gel be pressed through a 0.9 mm injection cannula. When the gel was injected into water, the gel did not spontaneously mix with water, but remained visually distinguishable.

Example 5

| Raw material | Per tablet | Complete batch |
|---|---|---|
| Tramadol hydrochloride | 50 mg | 100 g |
| Polyethylene oxide, NF, MW 7 000 000 (Polyox WSR 303, Dow Chemicals) | 90 mg | 180 g |
| Xanthan, NF | 10 mg | 20 g |
| Total weight | 300 mg | 300 g |

Tramadol hydrochloride, xanthan and polyethylene oxide were mixed in a free-fall mixer. A tabletting tool with a top punch, bottom punch and die for oblong tablets 10 mm in length and 5 mm in width was heated to 90° C. in a heating cabinet. 150 mg portions of the powder mixture were pressed with the heated tool, wherein pressure was maintained for at least 15 seconds by clamping the tabletting tool in a vice.

The breaking strength of the tablets was determined with the stated apparatus in accordance with the stated method. The tablets did not break when exposed to a force of 500 N. The tablets did suffer a little plastic deformation.

In vitro release of the active ingredient was determined as in Example 1 and was:

| Time | Released quantity |
|---|---|
| 30 min | 22% |
| 120 min | 50% |
| 240 min | 80% |
| 360 min | 90% |
| 480 min | 99% |

The tablets could be cut up into pieces of an edge length of as small as approx. 2 mm, but could not be pulverised. When the pieces are combined with water, a highly viscous gel is formed. Only with great difficulty could the gel be pressed through a 0.9 mm injection cannula. When the gel was injected into water, the gel did not spontaneously mix with water, but remained visually distinguishable.

Example 6

A tablet with the following composition was produced as described in Example 1:

| Components | Per tablet | Per batch |
|---|---|---|
| Oxycodone hydrochloride | 20.0 mg | 0.240 g |
| Xanthan, NF | 20.0 mg | 0.240 g |
| Polyethylene oxide, NF, MFI (190° C. at 21.6 kg/10 min) <0.5 g MW 7 000 000 (Polyox WSR 303, Dow Chemicals) | 110.0 mg | 1.320 g |
| Total weight | 150.0 mg | 1.800 g |

Release of the active ingredient was determined as follows:

In vitro release of the active ingredient from the preparation was determined in a paddle stirrer apparatus in accordance with Pharm. Eur. The temperature of the release medium was 37° C. and the rotational speed 75 rpm. The phosphate buffer, pH 6.8, described in DSP served as the release medium. The quantity of active ingredient present in the solvent at the particular time of testing was determined by spectrophotometry.

| Time | Mean |
|---|---|
| 0 min | 0% |
| 30 min | 17% |
| 240 min | 61% |
| 480 min | 90% |
| 720 min | 101.1% |

The breaking strength of the tablets was determined with the stated apparatus in accordance with the stated method. The tablets did not break when exposed to a force of 500 N.

The tablets could be cut up into pieces of an edge length of as small as approx. 2 mm, but could not be pulverised. When the pieces are combined with water, a highly viscous gel is formed. Only with great difficulty could the gel be pressed through a 0.9 mm injection cannula. When the gel was injected into water, the gel did not spontaneously mix with water, but remained visually distinguishable.

What is claimed is:

1. A thermoformed dosage form comprising:
   i) one or more active ingredients with abuse potential (A) selected from the group consisting of opiates and opioids,
   ii) optionally physiologically acceptable auxiliary substances (B),
   iii) at least 30% by weight of polyalkylene oxide (C) having a molecular weight of 1-15 million according to rheological measurements, and
   iv) optionally at least one wax (D),
wherein said dosage form has a breaking strength of at least 500 N and wherein the active ingredient with abuse potential (A) is present in a controlled release matrix of component (C).

2. The dosage form according to claim 1, which is in the form of a tablet.

3. The dosage form according to claim 1, wherein the wax (D) is at least one natural, semi-synthetic or synthetic wax with a softening point of at least 60° C.

4. The dosage form according to claim 3, wherein the wax (D) is carnauba wax or beeswax.

5. A process for the production of a dosage form according to claim 1, said process comprising mixing components (A), the optionally present component (B), component (C) and the optionally present component (D) to form a mixture and, optionally after granulation, press-forming the mixture with preceding, simultaneous, or subsequent exposure to heat.

6. A process according to claim 5, wherein granulation is performed by means of a melt process.

7. A dosage form obtained by the process of claim 5.

8. The dosage form according to claim 1, wherein the active ingredient with abuse potential (A) is oxycodone or a physiologically acceptable salt thereof.

9. The dosage form according to claim 1, wherein the active ingredient with abuse potential (A) is oxymorphone or a physiologically acceptable salt thereof.

* * * * *

UNITED STATES PATENT AND TRADEMARK OFFICE
CERTIFICATE OF CORRECTION

PATENT NO.      : 8,114,383 B2
APPLICATION NO. : 10/718112
DATED           : February 14, 2012
INVENTOR(S)     : Johannes Bartholomaus et al.

It is certified that error appears in the above-identified patent and that said Letters Patent is hereby corrected as shown below:

Column 19, line 55, "300 mg" should read -- 150 mg --.

Column 21, line 8, "30%" should read -- 60% --.

Signed and Sealed this
Fifteenth Day of January, 2013

David J. Kappos
*Director of the United States Patent and Trademark Office*